(12) United States Patent
Smith et al.

(10) Patent No.: US 11,432,863 B2
(45) Date of Patent: *Sep. 6, 2022

(54) WIRE PASSER SYSTEM AND METHOD

(71) Applicants: Judd Michael Smith, Lebanon, NH (US); Tadd Nicholas Smith, Rye, NH (US); C Daniel Smith, St. Joseph, MO (US)

(72) Inventors: Judd Michael Smith, Lebanon, NH (US); Tadd Nicholas Smith, Rye, NH (US); C Daniel Smith, St. Joseph, MO (US)

( * ) Notice: Subject to any disclaimer, the term of this patent is extended or adjusted under 35 U.S.C. 154(b) by 466 days.

This patent is subject to a terminal disclaimer.

(21) Appl. No.: 16/625,374

(22) PCT Filed: Jun. 20, 2018

(86) PCT No.: PCT/US2018/038572
§ 371 (c)(1),
(2) Date: Dec. 20, 2019

(87) PCT Pub. No.: WO2018/237055
PCT Pub. Date: Dec. 27, 2018

(65) Prior Publication Data
US 2021/0361335 A1   Nov. 25, 2021

Related U.S. Application Data

(63) Continuation of application No. 15/627,777, filed on Jun. 20, 2017, now Pat. No. 10,398,486.
(Continued)

(51) Int. Cl.
*A61B 17/88* (2006.01)
*A61B 17/17* (2006.01)
*A61B 17/82* (2006.01)

(52) U.S. Cl.
CPC ...... *A61B 17/8861* (2013.01); *A61B 17/1796* (2013.01); *A61B 17/82* (2013.01)

(58) Field of Classification Search
CPC ............ A61B 17/1796; A61B 17/1697; A61B 17/885; A61B 17/8869; A61B 17/0469;
(Continued)

(56) References Cited

U.S. PATENT DOCUMENTS

| 5,851,209 A | 12/1998 | Kummer et al. |
| 6,086,596 A | 7/2000 | Durham |

(Continued)

FOREIGN PATENT DOCUMENTS

| CN | 104546112 B | 10/2016 |
| WO | 2013/063145 A1 | 5/2013 |
| WO | 2017/075243 A1 | 5/2017 |

OTHER PUBLICATIONS

PCT Search Report and Written Opinion dated Oct. 4, 2018 for related PCT Patent Application No. PCT/US2018/038572, 13 pages.
(Continued)

*Primary Examiner* — Jessica Weiss
(74) *Attorney, Agent, or Firm* — Hovey Williams LLP; Kameron D. Kelly

(57) ABSTRACT

A wire passer system for passing a surgical wire around a bone. The wire passer system broadly comprises a gun assembly, a flexible push member, and a surgical wire. The gun assembly can comprise a handle, a trigger, a rigid guide section, a support guide, a push rod, and tensioner.

31 Claims, 7 Drawing Sheets

Related U.S. Application Data

(60) Provisional application No. 62/687,062, filed on Jun. 19, 2018, provisional application No. 62/583,955, filed on Nov. 9, 2017.

(58) Field of Classification Search
CPC ............ A61B 17/0482; A61B 17/0483; A61B 17/8861; A61B 17/82; A61B 17/823; A61B 17/7053; A61B 17/842
USPC .......................................... 606/103, 144–150
See application file for complete search history.

(56) References Cited

U.S. PATENT DOCUMENTS

| | | | |
|---|---|---|---|
| 10,398,486 B2 * | 9/2019 | Smith ................ | A61B 17/8861 600/546 |
| 2006/0015122 A1 | 1/2006 | Rupp | |
| 2006/0258951 A1 * | 11/2006 | Bleich ................ | A61B 17/8861 600/546 |
| 2007/0038230 A1 | 2/2007 | Stone et al. | |
| 2007/0185532 A1 * | 8/2007 | Stone ................ | A61B 17/0482 606/232 |
| 2012/0232567 A1 * | 9/2012 | Fairneny ............ | A61B 17/0482 606/147 |
| 2015/0313656 A1 * | 11/2015 | Hulliger ................ | A61B 17/82 606/74 |
| 2018/0360517 A1 * | 12/2018 | Smith ................ | A61B 17/8861 600/546 |

OTHER PUBLICATIONS

International Search Report and Written Opinion for related PCT Patent Application No. PCT/US2018/038572 dated Oct. 4, 2018, 13 pages.

\* cited by examiner

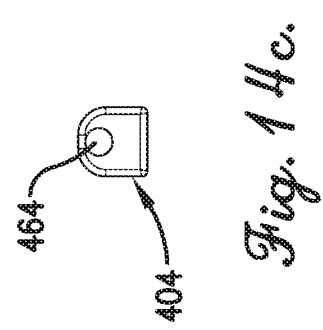
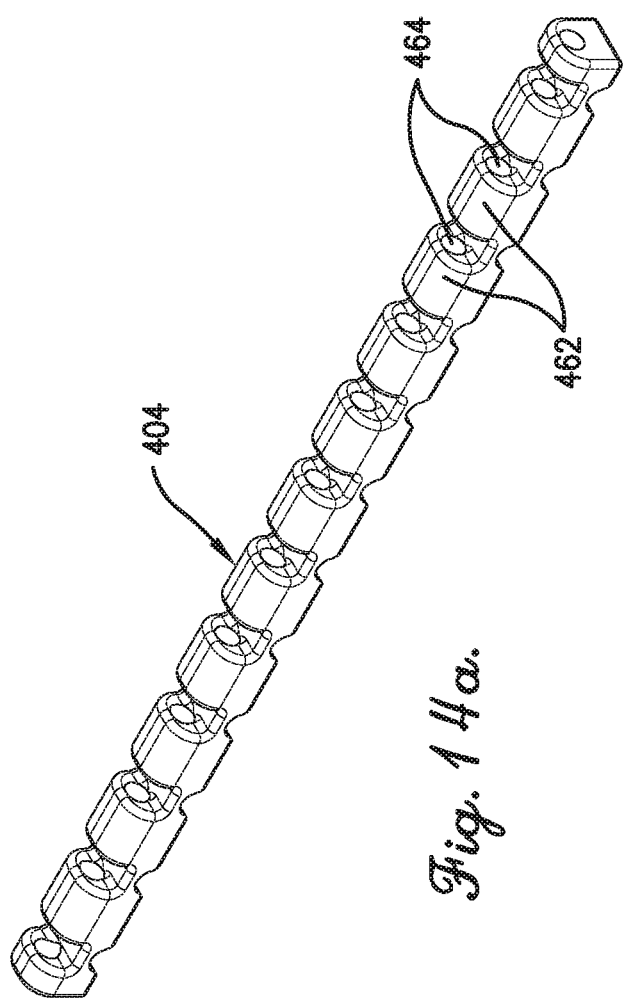
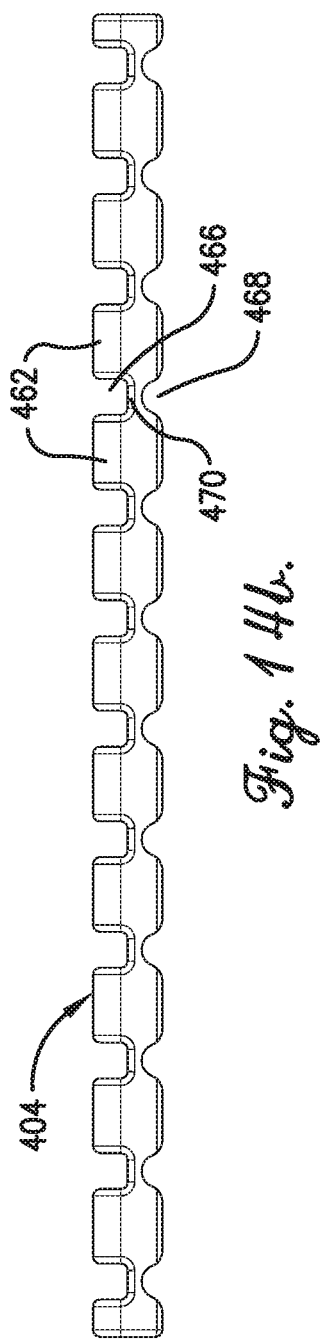

WIRE PASSER SYSTEM AND METHOD

RELATED APPLICATIONS

This application is a national stage application, under 35 U.S.C. § 371 of International Patent Application No. PCT/US2018/038572, filed on Jun. 20, 2018 and published as WO 2018/237055 on Dec. 27, 2018, which claims priority to (1) U.S. patent application Ser. No. 15/627,777, filed Jun. 20, 2017; (2) U.S. Provisional Patent Application No. U.S. Provisional Application No. 62/583,955, filed Nov. 9, 2017; and (3) U.S. Provisional Application No. 62/687,062, filed Jun. 19, 2018, which are all hereby incorporated by reference in their entirety.

BACKGROUND

Bone fractures such as subtrochanteric and periprosthetic fractures often require surgery in which a bone brace or splint is attached to two or more fractured bone segments via surgical wire. Surgical wire passers are often used for guiding the surgical wire around the bone segments. Unfortunately, conventional surgical wire passers are unwieldy and often cause significant blood loss and soft tissue trauma as they are maneuvered around the bone. This is particularly exacerbated with large, unhealthy, and frail patients in which extra or extremely delicate soft tissue must be handled. The prolonged operation time increases post-operative morbidity and mortality. Furthermore, orthopedic trauma surgery is often conducted during evening hours or on weekends with inexperienced or overworked hospital staff, thus increasing the chances of inadvertent surgical complications resulting from the use of conventional surgical wire passers.

SUMMARY

Embodiments of the present invention solve the above-described problems and provide a distinct advance in surgical tools. An embodiment of the invention is an articulating wire passer broadly comprising a handle, a rigid guide section, a support guide, a trigger, a push rod, an articulable member, a tensioner, and a wire catcher.

The handle allows a user to grip the articulating wire passer and direct the articulable member towards a bone. The handle may have a pistol grip shape, a T-shape, or any other suitable shape and may have a protrusion, ergonomic gripping contours, ridges, or other geometry for allowing the user to firmly grasp the articulating wire passer.

The rigid guide section includes a channel, a number of forward facing ratchet teeth, and a ratchet guide. The channel guides the push rod and articulable member and is an open-topped U-shaped or C-shaped chute. The forward facing ratchet teeth are aligned with the channel for engaging a pawl of the push rod. The ratchet guide is configured to receive a guide pin of a pawl of the trigger and is a groove, slot, cam, or similar feature for allowing the pawl of the trigger to pivot into engagement with ratchet teeth of the push rod and shift the push rod forward.

The support guide has a curved front surface and a rear tip guide. The support guide abuts the bone and the tip guide directs the end segment of the articulable member towards the wire catcher after the end segment passes around the bone.

The trigger allows the user to advance the articulable member from an extended position to an engaged position and includes a return spring and a pawl. The return spring is connected between the trigger and the handle for urging the trigger to a released position when a squeezing force is removed from the trigger and handle. The pawl is configured to ratchetably engage ratchet teeth of the push rod and includes a guide pin or similar feature for following the ratchet guide of the rigid guide section and a release for disengaging the pawl from the ratchet teeth of the push rod. The trigger is pivotably connected to the handle near a top of the trigger so as to form a fulcrum point such that the squeezing force urges the pawl against the ratchet teeth of the push rod.

The push rod is an elongated member including a number of rear-facing ratchet teeth and a pawl. The rear-facing ratchet teeth are configured to be engaged by the pawl of the trigger. The pawl of the push rod is configured to engage the forward-facing ratchet teeth of the rigid guide section and may include a release for disengaging the pawl from the forward-facing ratchet teeth. The push rod is pivotably connected to the first segment of the articulable member at a distal end of the push rod.

The articulable member guides the surgical wire around the bone and comprises a number of segments pivotably connected to each other. The segments each include opposing top and bottom sides and opposing aft and forward ends. The forward ends are pivotably connected to aft ends of adjacent segments via pivot points on the top sides and are indented or stepped for interconnecting with adjacent segments to enhance lateral stability. A first end segment is pivotably connected to the distal end of the push rod. The distal end segment has a concave curved bottom side for following a convex contour of the bone and a convex curved top side. That is, the distal end segment is tapered for allowing the articulable member to be directed between the bone and non-skeletal body mass near the bone and pointed for penetration through fascial tissues. The end segment also has geometry for retaining an end stopper of the surgical wire therein. The segments and the push rod cooperatively form a longitudinal wire passageway configured to receive the surgical wire therein.

The tensioner includes a tensioning spring and a wire lock. The tensioning spring exerts a tensioning force on the surgical wire and is interchangeable for replacing a worn-out spring or for changing the amount of tension applied to the surgical wire for different applications. The wire lock engages the surgical wire and is a pivotable friction cam, clamp, or other similar locking mechanism.

The wire catcher includes a latch configured to engage the end of the surgical wire and a protrusion for allowing the user to push the wire catcher towards the tip guide and pull the wire catcher backwards after it catches the surgical wire. The wire catcher is slideably attached to an underside of the rigid guide section of the handle.

In use, the surgical wire is inserted through the wire passageway of the push rod and articulable member such that the end stopper of the surgical wire is retained by the end stopper engaging geometry of the end segment. The tensioning spring of the tensioner is optionally pre-compressed a desired amount. The wire lock is then shifted into engagement with the surgical wire regardless of whether the tensioning spring has been pre-compressed. The articulating wire passer is then positioned such that the curved surface of the support guide rests against the bone.

The trigger is then squeezed such that the pawl of the trigger urges the push rod and articulable member forward a small amount along the channel of the rigid guide section via the ratchet teeth of the push rod. That is, the pawl of the push rod passively slides over the ratchet teeth of the rigid guide section as the push rod is moved forward and engages one of ratchet teeth when the push rod and articulable member stop advancing, which prevents the push rod and articulable member from backtracking.

The end segment of the articulable member pulls the surgical wire and hence the wire lock forward via the end stopper engaging geometry. This compresses the tensioning spring, which induces or increases tension in the surgical wire. The tension in the surgical wire causes segments to pivot relative to adjacent segments around the bone as they emerge from the distal end of the channel. The free segments may pivot to a predetermined relative angle dictated by the shape of the segments or a desired relative angle according to a wire tension induced by the tensioner.

The trigger is then released such that the return spring urges the trigger back to a relaxed position. The pawl of the trigger passively slides over the ratchet teeth of the push rod as the trigger returns to the relaxed position and engages one of the ratchet teeth when the trigger is stopped or reaches the relaxed position. The trigger is repeatedly squeezed and released such that the articulable member curls around the bone from an extended position to an engaged position as the articulable member and push rod are ratcheted forward.

The end segment pierces and/or passes between soft tissues and draws the surgical wire around the bone as the articulable member advances. The end section then advances along the tip guide of the support guide towards the wire catcher on the other side of the bone.

The wire catcher is then shifted forward along the underside of the rigid guide section until the latch has moved past the end stopper of the surgical wire. The wire catcher is then shifted backwards along the underside of the rigid guide section such that the latch engages the end stopper of the surgical wire. Alternatively, the latch may automatically engage the end stopper when the wire catcher is shifted forward.

The release of the trigger is then depressed or rotated to disengage the pawl of the trigger from the ratchet teeth of the push rod and the release of the push rod is depressed or rotated to disengage the pawl of the push rod from the ratchet teeth of the rigid guide section. The push rod and articulable member are then shifted backwards towards the tensioner such that the segments shift back around the bone from the engaged position to the extended position. The surgical wire stays wrapped around the bone because the end stopper of the surgical wire is in engagement with the latch of the wire catcher. The surgical wire is then clamped to form a construct that encircles the bone, which can be used alone or in combination with plates, rods, or other methods of bone fixation. The articulating wire passer is then repositioned laterally along the bone for passing additional surgical wire around the bone.

The above-described articulating wire passer provides several advantages over conventional wire passers. For example, the articulable member curls around the bone due to tension in the surgical wire, thus ensuring that the disturbance of non-skeletal body mass near the bone is minimized. The articulating wire passer also allows the surgical wire to be passed around the bone without the handle being moved significantly within the operating area. This reduces the surgical exposure and total space required to complete the surgery and reduces the likelihood of damaging non-skeletal body mass. The support guide allows the user to position the articulating wire passer against the bone properly before passing the surgical wire around the bone, which increases repeatability and accuracy of the procedure while decreasing the amount of time required to complete the surgery.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

BRIEF DESCRIPTION OF THE DRAWINGS

FIGS. 14a-c are various views of a flexible push member suitable for use in the wire passer gun assembly depicted in FIG. 13.

Figure 1:
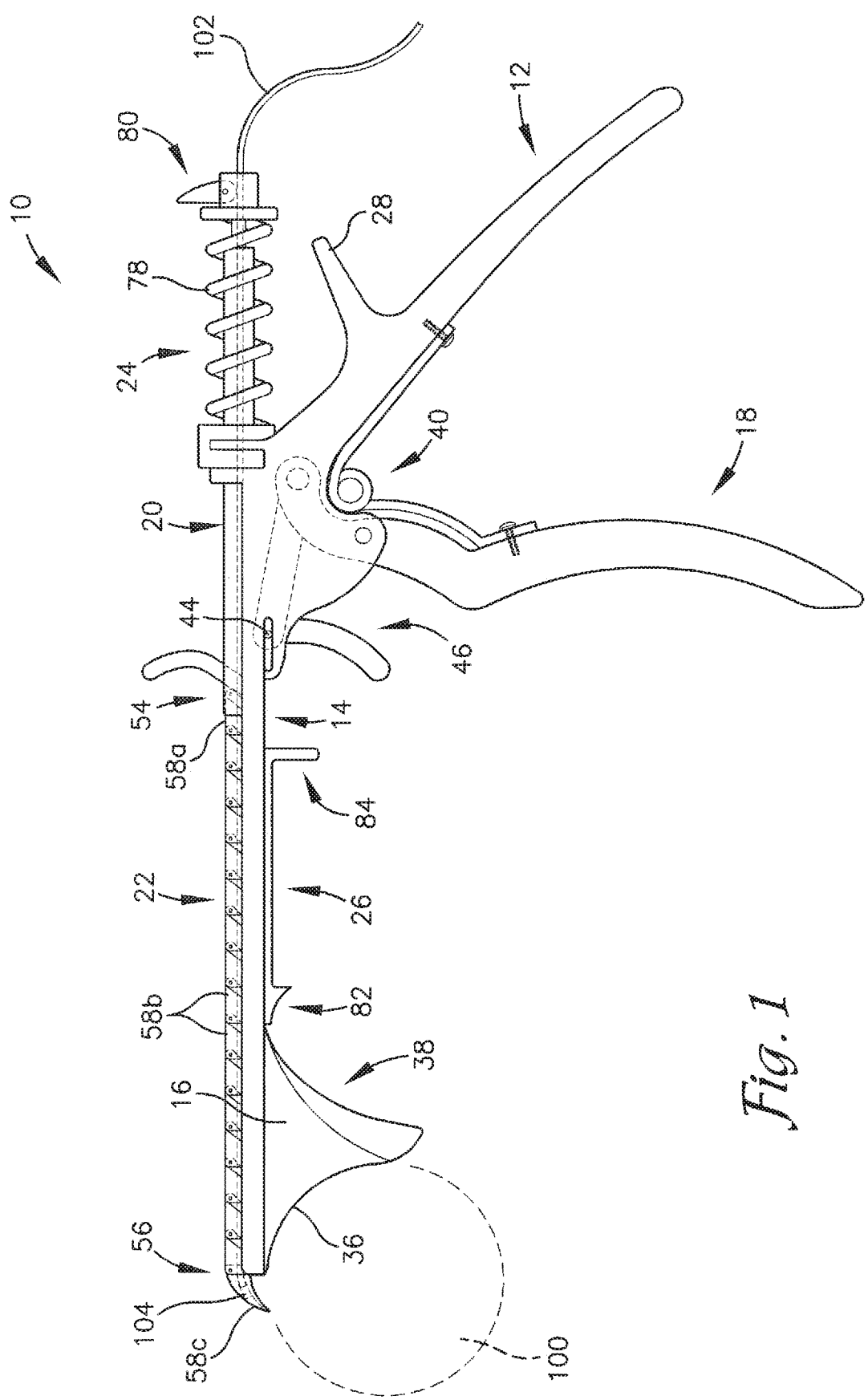
FIG. 1 is a side elevation view of an articulating wire passer constructed in accordance with an embodiment of the invention.
Figure 2:
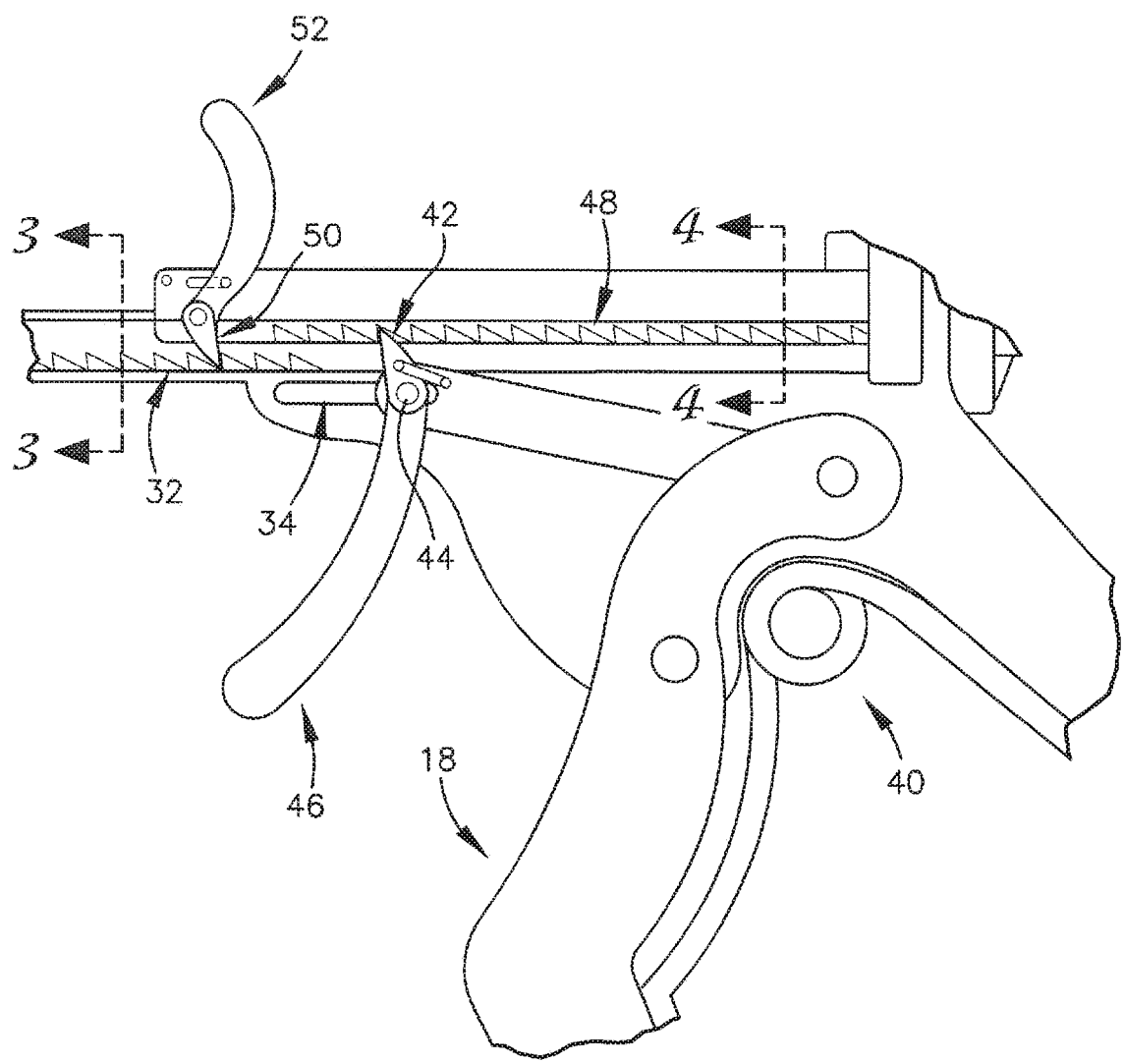
FIG. 2 is an enlarged side elevation view of a ratcheting mechanism of the articulating wire passer.
Figure 3:
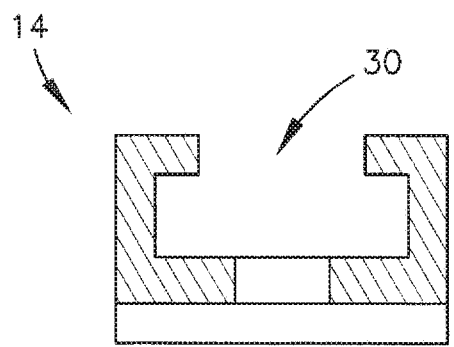
FIG. 3 is a sectional view of a channel of the articulating wire passer.
Figure 4:
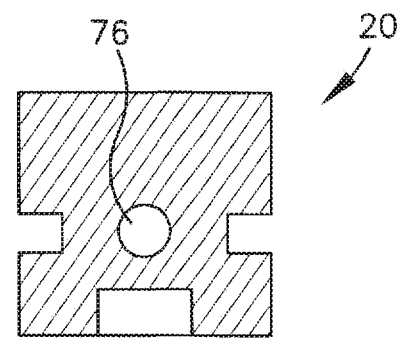
FIG. 4 is a sectional view of a push rod of the articulating wire passer.
Figure 5:
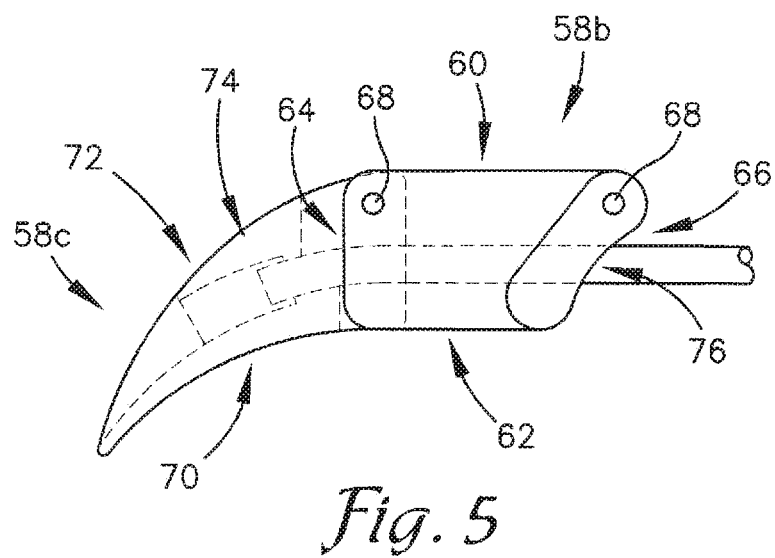
FIG. 5 is a side elevation view of segments of an articulable member of the articulating wire passer.
Figure 6:
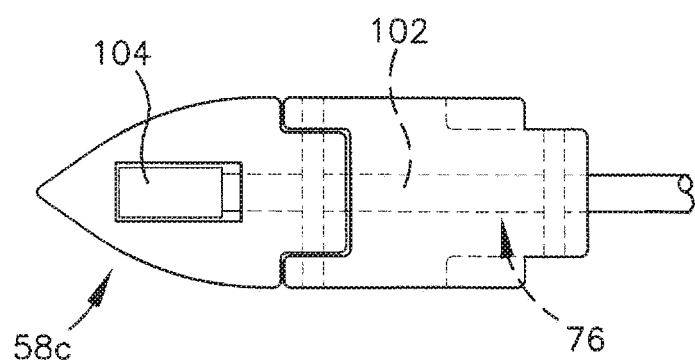
FIG. 6 is a top plan view of the segments of FIG. 5.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention may be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to the drawing figures, an articulating wire passer 10 is illustrated in accordance with embodiments of the invention. The articulating wire passer 10 broadly comprises a handle 12, a rigid guide section 14, a support guide 16, a trigger 18, a push rod 20, an articulable member 22, a tensioner 24, and a wire catcher 26.

The handle 12 allows a user to grip the articulating wire passer 10 and direct the articulable member 22 towards a bone 100. The handle 12 may have a pistol grip shape, a T-shape, or any other suitable shape and may have a protrusion 28, ergonomic gripping contours, ridges, or other geometry for allowing the user to firmly grasp the articulating wire passer 10.

The rigid guide section 14 extends forward from the handle 12 and may include a channel 30, a number of forward facing ratchet teeth 32, and a ratchet guide 34. The channel 30 guides the push rod 20 and articulable member 22 and may be enclosed or an open-topped U-shaped or C-shaped guide. The forward facing ratchet teeth 32 are aligned with the channel 30 for engaging a pawl of the push rod 20. The ratchet guide 34 is configured to receive a guide pin of a pawl of the trigger 18 and may be a groove, slot, cam, or similar feature for allowing the pawl of the trigger 18 to pivot into engagement with ratchet teeth of the push rod 20 and shift the push rod 20 forward.

The support guide 16 extends from a distal end of the rigid guide section 14 and may have a curved surface 36 for abutting the bone 100. The support guide 16 may also have a tip guide 38 for guiding the end segment of the articulable member 22 towards the wire catcher 26 after the end segment passes around the bone 100.

The trigger 18 allows the user to advance the articulable member 22 from an extended position to an engaged position and includes a return spring 40 and a pawl 42. The return spring 40 is connected between the trigger 18 and the handle 12 for urging the trigger 18 to a released position when a squeezing force is removed from the trigger 18 and handle 12. The return spring 40 may be a leaf spring, coil spring, torsion spring, or any other suitable spring. The pawl 42 is configured to ratchetably engage ratchet teeth of the push rod 20 and may include a guide pin 44 or similar feature for following the ratchet guide 34 of the rigid guide section 14 and a release 46 for disengaging the pawl 42 from the ratchet teeth of the push rod 20. The trigger 18 may be pivotably connected to the handle 12 near a top of the trigger 18 so as to form a fulcrum point such that the squeezing force urges the pawl 42 against the ratchet teeth of the push rod 20.

The push rod 20 may be an elongated member including a number of rear-facing ratchet teeth 48 and a pawl 50. The rear-facing ratchet teeth 48 are configured to be engaged by the pawl 42 of the trigger 18. The pawl 50 is configured to engage the forward-facing ratchet teeth 32 of the rigid guide section 14 and may include a release 52 for disengaging the pawl 50 from the forward-facing ratchet teeth 32. The push rod 20 may be pivotably connected to the first segment of the articulable member 22 at a distal end of the push rod 20 and may be slotted or otherwise shaped for being retained in the channel 30 of the rigid guide section 14.

The articulable member 22 guides the surgical wire 102 around the bone 100 and includes opposing aft and forward ends 54, 56. The articulable member 22 comprises a first end segment 58a, a number of intermediate segments 58b, and a second or distal end segment 58c (at least 5 segments, preferably at least 8 segments, and more preferably at least 10 segments in total) pivotably connected to each other. The segments 58a-c each include opposing top and bottom sides 60, 62 and opposing aft and forward ends 64, 66. The forward ends 66 are pivotably connected to aft ends 64 of adjacent segments 58a-c via pivot points 68 on the top sides 60 and may be indented or stepped for aligning with aft ends 64 of adjacent segments 58a-c and for pivoting relative to adjacent segments 58a-c a predetermined amount (at least 20 degrees, preferably at least 30 degrees, and more preferably at least 45 degrees). The first end segment 58a may be pivotably connected to the distal end of the push rod 20. The distal end segment 58c may have a concave curved bottom side 70 for following a convex contour of the bone 100 and a convex curved top side 72 such that the distal end segment 58c is tapered for allowing the articulable member 22 to be directed between the bone 100 and non-skeletal body mass near the bone 100. The end segment 58c may also be pointed for penetration through fascial tissues. The end segment 58c may also have end stopper engaging geometry 74 for retaining an end stopper 104 of the surgical wire 102 therein. The segments 58a-c may be slotted or otherwise shaped for being retained in the channel 30 of the rigid guide section 14. The segments 58a-c and the push rod 20 cooperatively form a longitudinal wire passageway 76 configured to receive the surgical wire 102 therein. The articulable member 22 is configured to be selectively shifted between an extended position and an engaged position as described in more detail below.

The tensioner 24 induces tension on the surgical wire 102 and may include a tensioning spring 78 and a wire lock 80. The tensioning spring 78 and/or tensioner 24 as a whole may be interchangeable for replacing a worn-out spring or for changing a tension force range of the articulating wire passer 10 for different applications. The wire lock 80 engages the surgical wire 102 and may be a pivotable friction cam, clamp, or other similar locking mechanism.

The wire catcher 26 includes a latch 82 configured to engage the end of the surgical wire 102 and a protrusion 84 for allowing the user to push the wire catcher 26 towards the tip guide 38 and pull the wire catcher 26 after it catches the surgical wire 102. The wire catcher 26 may be slideably attached to an underside of the rigid guide section 14 of the handle 12.

Use of the articulating wire passer 10 will now be described in more detail. First, the surgical wire 102 may be inserted through the wire passageway 76 of the push rod 20 and articulable member 22 such that the end stopper 104 of the surgical wire 102 is retained by the end stopper engaging geometry 74 of the end segment 58c. The tensioning spring 78 of the tensioner 24 may optionally be pre-compressed a desired amount. The wire lock 80 may then be shifted into engagement with the surgical wire 102. The articulating wire passer 10 may then be positioned such that the curved surface 52 of the support guide 18 rests against the bone 100.

The trigger 18 may then be squeezed such that the pawl 42 of the trigger 18 urges the push rod 20 and articulable member 22 forward a small amount (at least 0.25 inches, preferably at least 0.5 inches, and more preferably at least 1 inch) along the channel 30 of the rigid guide section 14 via the ratchet teeth 48 of the push rod 20. The pawl 50 of the push rod 20 passively slides over the ratchet teeth 32 of the rigid guide section 14 as the push rod 20 is moved forward and engages one of ratchet teeth 32 when the push rod 20 and articulable member 22 stop advancing, which prevents the push rod 20 and articulable member 22 from backtracking.

The end segment 58c of the articulable member 22 pulls the surgical wire 102 and hence the wire lock 80 forward via the end stopper engaging geometry 74. This compresses the tensioning spring 78, which induces or increases tension in the surgical wire 102. The tension in the surgical wire 102 causes segments (e.g., end segment 58c) to pivot relative to the next segment (e.g., adjacent segment 58b) around the bone 100 as they emerge from the distal end of the channel 30. The free segments may pivot to a predetermined relative angle (at least 20 degrees, preferably at least 30 degrees, and more preferably at least 45 degrees) dictated by the shape of the segments 58a-c or a desired relative angle according to a wire tension induced by the tensioner 24.

The trigger 18 may then be released such that the return spring 40 urges the trigger 18 back to a relaxed position. The pawl 42 of the trigger 18 passively slides over the ratchet teeth 48 of the push rod 20 as the trigger 18 returns to the relaxed position and engages one of the ratchet teeth 48 when the trigger 18 is stopped or reaches the relaxed position. The trigger 18 may be repeatedly squeezed and released such that the articulable member 22 curls around the bone 100 from an extended position to an engaged position as the articulable member 22 and push rod 20 are ratcheted forward.

The end segment 58c pierces and/or passes between soft tissues (such as the intermuscular septum of the thigh) and draws the surgical wire 102 around the bone 100 as the articulable member 22 advances. The end section 58c then advances along the tip guide 38 of the support guide 16 towards the wire catcher 26 on the other side of the bone 100.

The wire catcher 26 may then be shifted forward along the underside of the rigid guide section 14 until the latch 82 has moved past the end stopper 104 of the surgical wire 102. The wire catcher 26 may then be shifted backwards along the underside of the rigid guide section 14 such that the latch 82 engages the end stopper 104 of the surgical wire 102. Alternatively, the latch 82 may automatically engage the end stopper 104 when the wire catcher 26 is shifted forward.

The release 46 of the trigger 18 may be depressed or rotated to disengage the pawl 42 of the trigger 18 from the ratchet teeth 48 of the push rod 20 and the release 52 of the push rod 20 may be depressed or rotated to disengage the pawl 50 of the push rod 20 from the ratchet teeth 32 of the rigid guide section 14. The push rod 20 and articulable member 22 may then be shifted backwards towards the tensioner 24 such that the segments 58a-c shift back around the bone 100 from the engaged position to the extended position. The surgical wire 102 stays wrapped around the bone 100 because the end stopper 104 of the surgical wire 102 is in engagement with the latch 82 of the wire catcher 26. The surgical wire 102 may then be clipped between approximately 2 inches and 5 inches (depending on the diameter of the bone 100) from its end to form a wire piece. The wire piece may then be clamped to form a construct that encircles the bone, which can be used alone or in combination with plates, rods, or other methods of bone fixation. The articulating wire passer 10 may then be repositioned laterally along the bone 100 for passing additional surgical wire around the bone 100.

The above-described articulating wire passer 10 provides several advantages over conventional wire passers. For example, the articulating member 22 curls around the bone 100 due to tension in the surgical wire 102, thus ensuring that the disturbance of non-skeletal body mass near the bone 100 is minimized. The articulating wire passer 10 also allows the surgical wire 102 to be passed around the bone 100 without the handle 12 being moved significantly within the operating area. This reduces the surgical exposure and total space required to complete the surgery and reduces the likelihood of damaging non-skeletal body mass. The support guide 16 allows the user to position the articulating wire passer 10 against the bone 100 properly before passing the surgical wire 102 around the bone 100, which increases repeatability and accuracy of the procedure while decreasing the amount of time required to complete the surgery.

FIGS. 7-12 show an alternative embodiment of a wire passer system 300 that can provide enhanced sterility, simplicity, and ease of use by employing multiple single-use components. Such single-use components do not need to be washed and sterilized between each procedure. Rather, the single-use components can be purchased in sterile packaging and opened immediately prior to use; thereby, virtually eliminating the risk of inadequate sterilization of such components.

Figure 7:
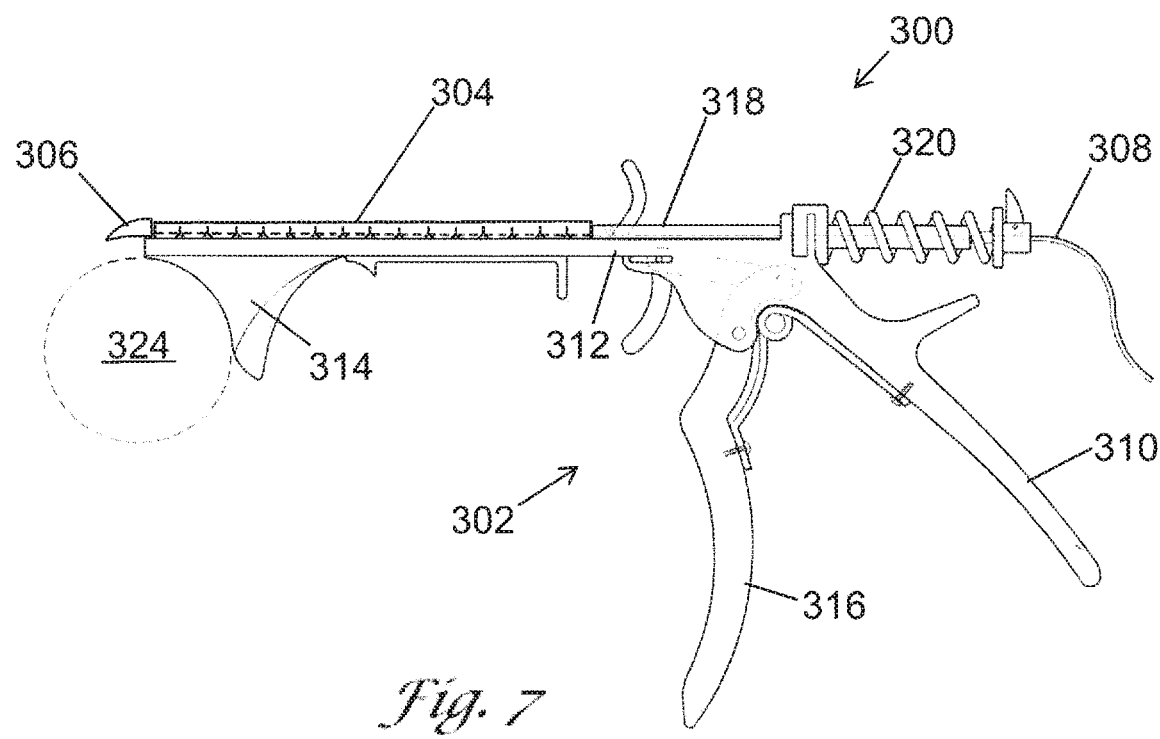
FIG. 7 is a side elevation view of a wire passer system constructed in accordance with an alternative embodiment of the present invention, particularly illustrating the wire passer system in an initial configuration before extension around the bone.
Figure 8:
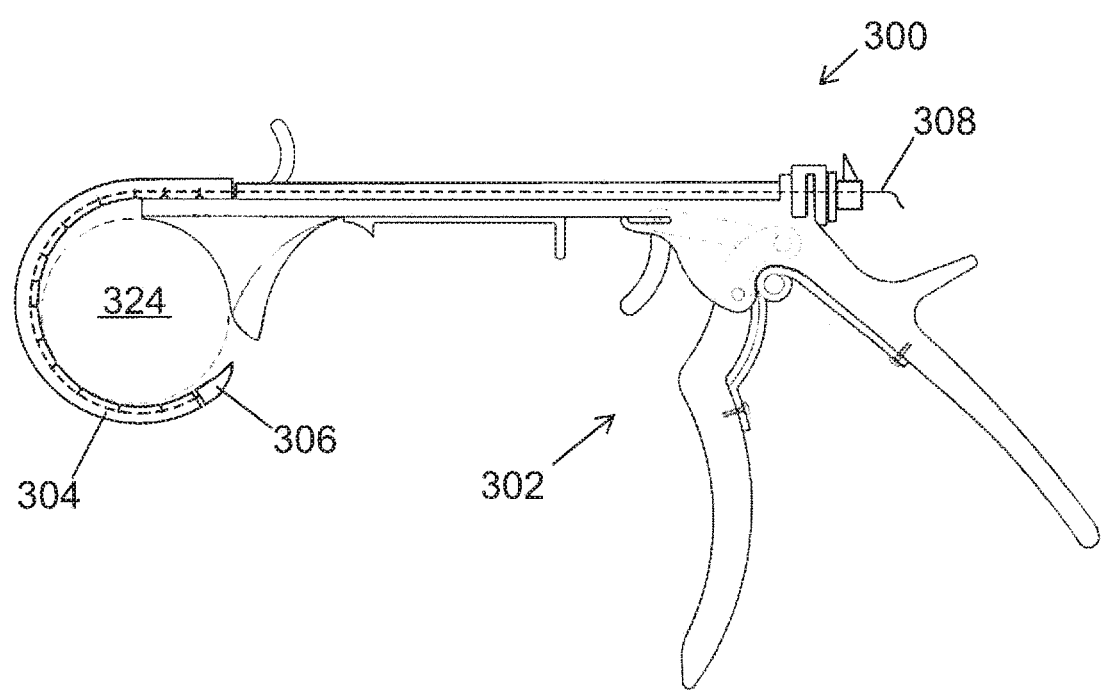
FIG. 8 is a side elevation view of the wire passer system of FIG. 7 in an extended configuration, with the tip member having been pushed around the bone and the surgical wire and push member being partially extended around the bone.

The wire passer system 300 depicted in FIGS. 7 and 8 includes four main components: 1) a gun assembly 302, 2) a flexible push member 304, 3) a tip member 306, and 4) a surgical wire 308. Similar to the wire passer 100 depicted in FIG. 1, the gun assembly 302 depicted in FIGS. 7 and 8 can include a handle 310, a rigid guide section 312, a support guide 314, a trigger 316, a push rod 318, and a tensioner 320.

In certain embodiments, the gun assembly 302 is reusable, while the flexible push member 304, the tip member 306, and the surgical wire 308 are all single-use items. In such a configuration, the only component of the wire passer system 300 that needs cleaning and sterilization between procedures is the reusable gun assembly 302, which has only minimal contact with the patient's body during surgical procedures. The other components of the wire passer system 300 (i.e., the push member 304, the tip member 306, and the surgical wire 308) are all single-use items that can be provided in sterile packaging for opening immediately prior to a procedure.

In certain embodiments, the flexible push member 304, the tip member 306, and the surgical wire 308 can all be packaged together in a single sterile package (not shown). Alternatively, the flexible push member 304 can be packaged in one sterile package, while the tip member 306 and surgical wire 308 are combined in another sterile package. Further, each of the flexible push member 304, the tip member 306, and the surgical wire 308 can be provided in its own individual sterile package.

The flexible push member 304 shown in FIGS. 7 and 8 is formed of a resilient material. The resilient material can be a synthetic resin, such as, for example, ABS plastic. The flexible push member 304 can be in the form of a monolithic body that is molded from a single material. The material forming the flexible push member 304 can have a flexural modulus (ASTM D790) of 1 to 5 GPa, 1.5 to 4 GPa, or 2 to 3 GPA. The material forming the flexible push member 304 can have a flexural strength (ASTM D790) of 40 to 150 MPa, 50 to 100 MPa, or 60 to 90 MPa.

As shown in FIG. 8, the resiliency of the push member 304 can allow it to bend in a "living hinge" manner when it passes around a bone 324. As shown in FIGS. 7 and 8, the top side of the flexible push member 304 can be continuous, while the bottom side (i.e., bone-contacting side) can include a plurality of openings (e.g., notches and/or slots) to facilitate flexing of the push member 304 around the bone 324. Since the flexible push member 304 can be formed of a relatively inexpensive material, it can be a disposable (i.e., single use) item.

The flexible push member 304 includes a longitudinally extending internal passageway for receiving the surgical wire 308. As shown in FIGS. 7 and 8, the flexible push member 304 is disposed between the push rod 318 of the gun assembly 302 and the tip member 306. As the push rod 318 is advanced by squeezing the trigger 316, the push rod 318 pushes the flexible push member 304, which in turn pushes the tip member 306. FIG. 8 shows that as the flexible push member 304 pushes the tip member 306 around the bone 324, the surgical wire 308, which is attached to the tip member 306 and extends through the longitudinal passageway in the flexible push member 304, is passed around the back side of the bone 324.

After the tip member 306 has passed around the back of the bone 324 and is exposed again at the front of the bone 324 (FIG. 8), the gun assembly 302 and flexible push member 304 can be decoupled from the tip member 306 and surgical wire 308 and removed from the surgical area. This can be accomplished by i) grasping and holding the tip member 306 at the front of the bone 324, ii) pulling the gun assembly 302 away from the surgical area and free of the surgical wire 308, and iii) pulling the flexible push member 304 out from around the bone 324, away from the surgical area, and free of the surgical wire 308.

Figure 9:
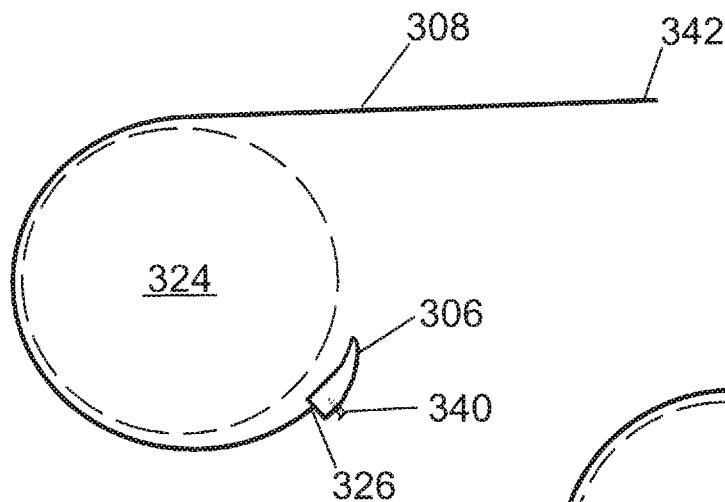
FIG. 9 is a side elevation view of the surgical wire and tip member extended around the bone, after removal of the gun assembly and flexible push member.

As depicted in FIG. 9, once the gun assembly 302 and flexible push member 304 have been removed from the surgical area, what remains is the surgical wire 308 extending around the back of the bone 324 and the tip member 306 attached to a first end 326 of the surgical wire 308, with the tip member 306 being exposed at the front of the bone 324 and accessible to the surgeon.

Figure 10:
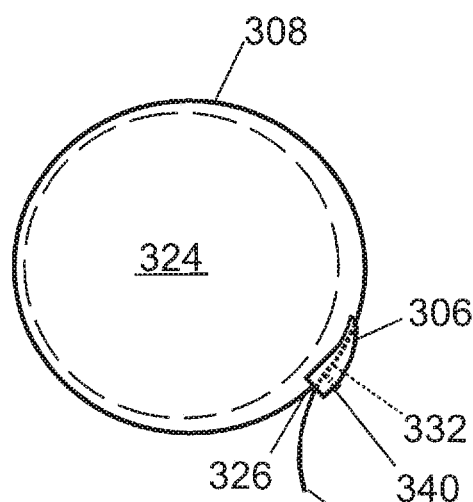
FIG. 10 is a side elevation view of the surgical wire and tip member in a tightened loop configuration around the bone, with the tip member securing the surgical wire in a loop.
Figure 11:
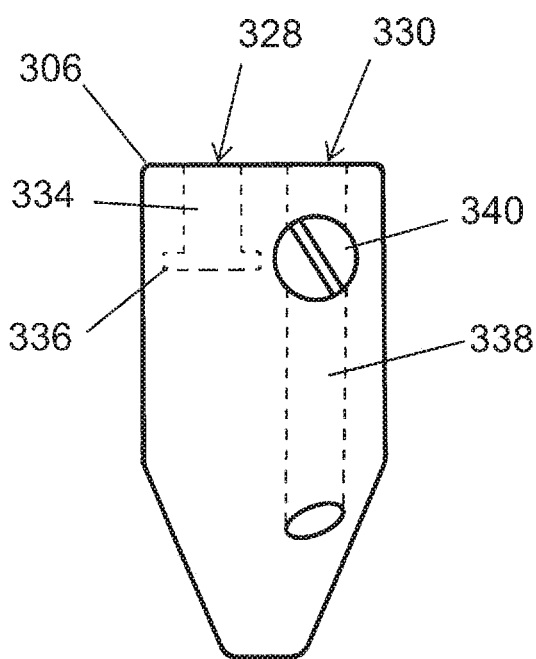
FIG. 11 is a top view of the tip member illustrated in FIGS. 7-10, particularly illustrating the two securement mechanisms used to connect the surgical wire to the tip member at different locations along the length of the surgical wire.
Figure 12:
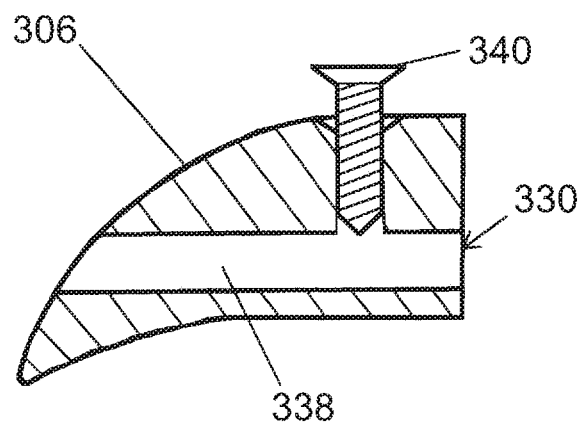
FIG. 12 is a side cross-sectional view of the tip member cut along a through-opening configured to receive a portion of the surgical wire, particularly illustrating a set screw used to secure the surgical wire in the through-opening to form the tightened loop of surgical wire around the bone.

As depicted in FIGS. 10-12, in certain embodiments, the tip member 306 is a multi-function member that is configured to both pull the surgical wire 308 around the bone 324 and to securely fix the surgical wire 308 around the bone 324 after the surgical wire 308 has been looped around the bone 324 and tightened. In such an embodiment, the tip member 306 acts as a coupling device for the surgical wire 308 and the tip member 306 remains in the human body (along with the surgical wire 308) after the procedure. As such, both the surgical wire 308 and the tip member 306 should be formed of a material (e.g., stainless steel) that minimizes the risk of infection or other negative reaction when left in the human body.

Thus, as shown in FIGS. 9-12, the tip member 306 can include a first securement mechanism 328 (FIG. 11) and a second securement mechanism 330 (FIGS. 11 and 12). The first securement mechanism 328 can be used to hold the first end 326 (FIGS. 9 and 10) of the surgical wire 308 during passage of the tip member 306 around the bone 324. The second securement mechanism 330 can be used to receive and hold a second portion 332 (FIG. 10) of the surgical wire 308 to thereby form a secure loop of the surgical wire 308 around the bone 324.

As shown in FIGS. 11 and 12, the first securement mechanism 328 can be formed of a first opening 334 that extends inwardly from the back of the tip member 306. The first opening 334 can include an enlarged section 336 spaced from the back of the tip member 306. The narrow section of the first opening 334 can receive a narrow portion of the first end 326 of the surgical wire 308. The enlarged section 336 of the first opening 334 can receive a broadened tip/flange (not shown) of the first end 326 of the surgical wire 308. The mating engagement between the broadened tip of the first end 326 of the surgical wire 308 and the enlarged section 336 of the first opening 334 can couple the surgical wire 308 to the tip member 306 and prevent the surgical wire 308 from pulling out of the tip member 306. The first securement mechanism 328 can form a pre-assembled permanent connection. Alternatively, the first securement mechanism 328 can form a releasable connection between the tip member 306 and the surgical wire 308. In other embodiments, the first end 326 of the surgical wire 308 can be permanently attached to the tip member 306 by welding, gluing, or soldering.

In certain embodiments, the second securement mechanism 330 of the tip member 306 includes a through-opening 338 and a set screw 340. As shown in FIGS. 9 and 10, the tip member 306 can be used to secure the surgical wire 308 in a loop around the bone 324 by i) inserting a free end 342 of the surgical wire 308 into the through-opening 338, ii) passing the free end 342 entirely through the through-opening 338, iii) pulling on the free end 342 of the surgical wire 308 to form a tightened loop of the surgical wire 308 around the bone 324, and iv) tightening the set screw 340 against the second portion 332 of the surgical wire 308 to thereby fix in the surgical wire 308 in a tightened loop around the bone 324 (FIG. 10).

To perform a surgical operation using the wire passer system 300 depicted in FIGS. 7-12, a surgeon can perform the following steps:

a) Create an incision that exposes a front side of the bone 324.

b) Open one or more sterile packages (not shown) containing the flexible push member 304, the tip member 306, and the surgical wire 308.

c) Load the flexible push member 304, the tip member 306, and the surgical wire 308 into the gun assembly 302 so the surgical wire 308 passes though the longitudinal passageway of the flexible push member 304 and the first end 326 of the surgical wire 308 is coupled to the tip member 306 by the first securement mechanism 328.

d) Engage a curved surface of the support guide 314 of the gun assembly 302 against the bone 324, with the tip member 306 being adjacent to the bone 324;

e) While the support guide 314 engages the bone 324, actuate the gun assembly 302 by repeatedly squeezing the trigger 316 of the gun assembly 302, thereby causing the push rod 318 of the gun assembly 302 to force the flexible push member 304 forward. The pushing forward of the flexible push member 304 causes the flexible push member 304 to curve around the bone 324, while pushing the tip member 306 around the bone 324.

f) Once the tip member 306 has been pushed around the back side of the bone 324 and is visible to the surgeon from the front side of the bone 324, remove the gun assembly 302 and push member 304 from the surgical wire 308, leaving the surgical wire 308 extending around the bone 324 and the tip member 306 exposed to the surgeon on the front side of the bone 324.

g) Pass the free end 342 of the surgical wire 308 through the through-opening 338 of the second securement mechanism 330 of the tip member 306 to create a loop of the surgical wire 308 around the bone 324.

h) Tighten the loop of surgical wire 308 around the bone 324 by pulling the free end 342 of the surgical wire 308, while the surgical wire 308 extends through the through-opening 338.

i) While the loop of surgical wire 308 around the bone 324 is tight, secure the second portion 332 of the surgical wire 308 to the tip member 306 by tightening the set screw 340 of the tip member 306 against the second portion 332 of the surgical wire 308.

j) Optionally, repeat steps b)-i) at different locations along the length of the bone 324.

k) Close the incision, leaving one or more loops formed of the surgical wire 308 and the tip member 306 in the patient's body.

l) Dispose of the used flexible push member(s) 304.

m) Wash and sterilize the gun assembly 302 for reuse.

Figure 13:
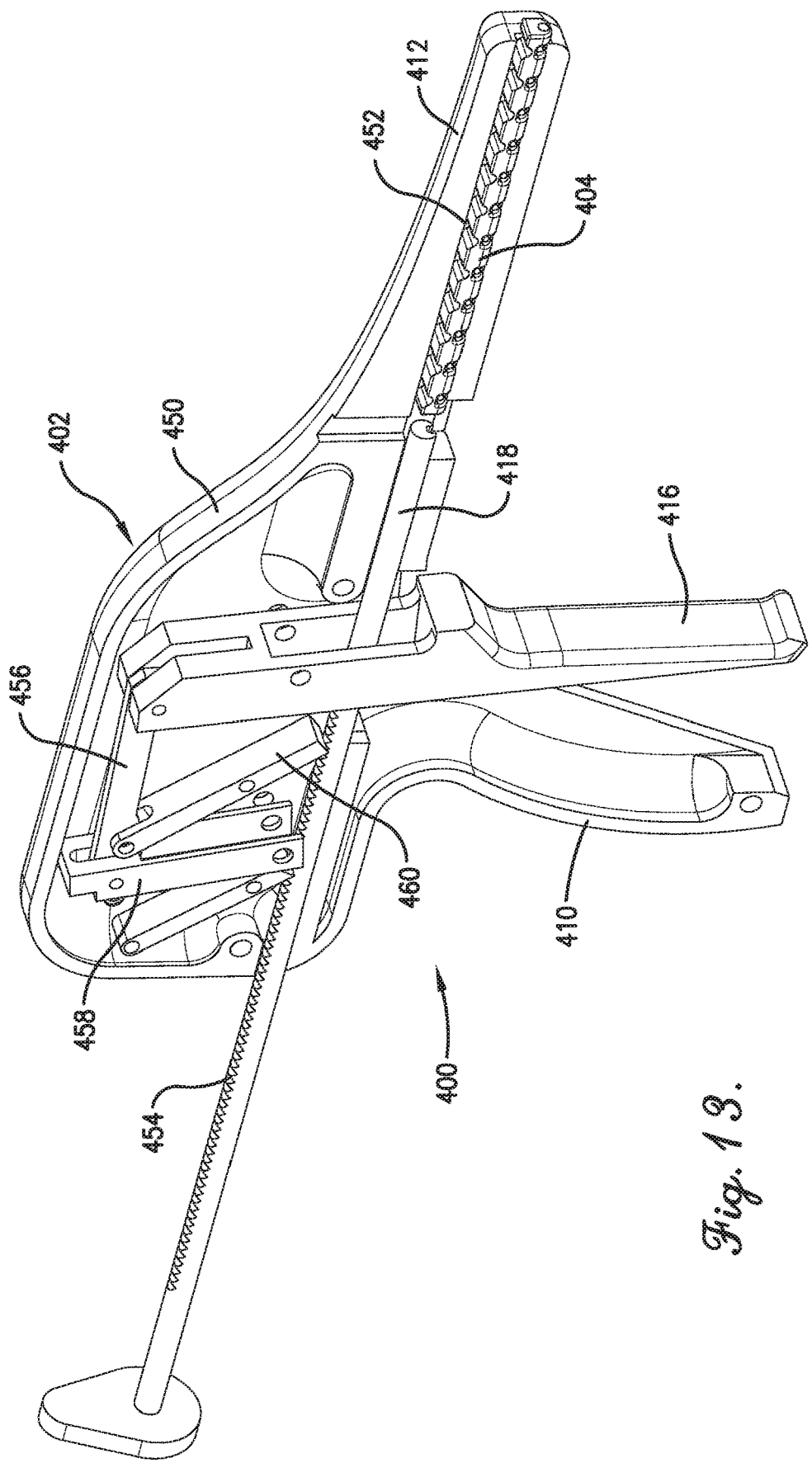
FIG. 13 is an isometric view of a wire passer system constructed in accordance with another alternative embodiment of the present invention, particularly illustrating the wire passer gun assembly with one-half of its housing being removed to reveal the internal components of the gun assembly.

FIG. 13 illustrates a wire passer system 400 having an alternative configuration, where the gun assembly 402 includes a different ratcheting mechanism for pushing forward a flexible push member 404 having a unique configuration. The gun assembly 402 of FIG. 13 include a housing 450, which provides the main structural support for the gun assembly 402, houses the internal pushing components of the gun assembly 402, and defines a guide passageway 452 within which the flexible push member 404 can be received and guided before and during deployment. In FIG. 13, one-half of the housing 450 has been removed, so that the internal components of the gun assembly 402 can be better illustrated.

The main components of the gun assembly 402 include the housing 450, a handle 410, a trigger 416, a rigid guide section 412, the guide passageway 452, a push rod 418 having a ratcheting section 454, a forward transfer member 456, a rock member 458, and a pawl member 460.

In operation, the flexible push member 404 can be loaded into the guide passageway 452 through the front opening of the guide passageway 452 at the tip of the gun assembly 402. Alternatively, the housing 450 and/or rigid guide section 412 can define an opening spaced from the tip of the gun assembly 402 through which the flexible push member 404 can be inserted and loaded into the guide passageway 452. In one embodiment, the flexible member 404 already has a surgical wire (not shown) loaded in the flexible member 404 when the flexible member 404 is inserted into the guide passageway 452. Before deploying the flexible member 404, the surgical wire can be coupled to a tensioner (not shown) that maintains tension in the surgical wire during deployment.

The flexible member 404 is deployed by repeated squeezing the trigger 416. It is preferred for full deployment of the flexible member 404 out of the guide passageway 452 to be accomplished in 2 to 12 full trigger squeezes, 3 to 10 full trigger squeezes, or 4 to 8 full trigger squeezes. When the trigger 416 is squeezed, the top portion of the trigger 416 moves forward, thereby shifting the forward transfer member 456 forward. The forward movement of the transfer member 456 pulls the top of the rock member 358 forward, thereby forcing the pawl member 460 forward as well. When the pawl member 460 is forced forward, the engagement tip of the pawl member 460 engages teeth of the serrated ratcheting section 454 of the push rod 418 and causes the push rod 418 to be pushed forward. A biasing member, such as a spring (not show), can be used to automatically return the trigger 416 to its initial forward position after the trigger 416 is squeezed. As the trigger 416 is moved forward by the biasing member (directly or indirectly), the engagement tip of the pawl member 460 passes rearwardly over a plurality of teeth of the ratcheting section 454 for engagement with rearward teeth spaced further from the tip of the push rod 418. Accordingly, by squeezing the trigger 416 multiple times, the flexible member 404 is passed out through the guide passageway 452 and deployed around the bone, as previously described.

FIGS. 14a-c show the flexible push member 404 that is configured to be used in conjunction with the gun assembly 402 depicted in FIG. 13. In FIG. 13, the flexible push member is show up-side-down to better illustrate its structural details. The flexible push member 404 can include a number of guide segments 462 connected by living hinge segments 470. Each guide segment 462 includes an opening 464 through which a surgical wire (not shown) can be passed. The openings 464 cooperatively for a longitudinal passageway through the flexible push member 404. The flexible push member 404 includes a plurality upper gaps 468 and lower gaps 466 defined between adjacent guide segments 462. The upper and lower gaps 468,466 are aligned in pairs along the length of the flexible push member 404, with each pair of upper and lower gaps 468,466 defining a living hinge segment 470 therebetween.

When the flexible push member 404 is deployed around a bone, tension on the surgical wire extending through the openings 464 in the guide segments 462 causes the flexible push member 404 to curl around the bone. This curling/bending of the flexible push member 404 is facilitated by the flexibility at the living hinge segments 470. When the flexible push member curls around the bone, the size of the lower gaps 466 decreases and the size of the upper gaps 468 increases, while the living hinge segment 470 is deformed. It is noted, however, it may be possible to form a flexible push member without any upper gaps, so that the living hinge segments are formed flush with the tops of the guide segments.

The wire passer system 400 depicted in FIGS. 13 and 14a-c can be used with the tips described above and can be packaged and used in the manner described above with respect to the wire passer system 300.

Although the invention has been described with reference to the exemplary embodiments illustrated in the attached drawings, it is noted that equivalents may be employed and substitutions made herein without departing from the scope of the invention as recited in the claims.

Having thus described various embodiments of the invention, what is claimed as new and desired to be protected by Letters Patent includes the following:

1. An articulating wire passer for passing a surgical wire around a bone, the articulating wire passer comprising:
    a gripping section configured to be grasped by a human hand;
    a rigid guide section coupled to and extending forward from the gripping section; and an articulable member configured to be slideable relative to the gripping section and guideable by the rigid guide section, wherein the articulable member comprises at least five segments pivotably connected to each other in series by a plurality of pivot points, wherein the segments form at least a portion of a wire passageway configured to receive at least a portion of the surgical wire therein such that the pivot points are offset from the wire passageway, and wherein the articulable member is shiftable between an extended position and an engaged position by pivoting the segments relative to each other at the pivot points via tension in the surgical wire.

2. The articulating wire passer of claim 1, further comprising a tensioner configured to engage and induce tension in the surgical wire.

3. The articulating wire passer of claim 1, further comprising a tip member attached to an end of the articulatable member, wherein the tip member has a tapered end for facilitating extension of the articulable member between the bone and a non-skeletal body mass near the bone.

4. The articulating wire passer of claim 3, wherein the tip member has a curved bottom side for following a convex contour of the bone.

5. The articulating wire passer of claim 1, wherein each of the pivot points is formed by a living hinge segment.

6. The articulating wire passer of claim 1, wherein the articulable member is a monolithic body formed of a single flexible material.

7. The articulating wire passer of claim 6, wherein the single flexible material is a synthetic resin having a flexural modulus of 1 to 5 GPa and a flexural strength of 40 to 150 MPa.

8. The articulating wire passer of claim 1, wherein the gripping section comprises a handle that extends transverse to a direction of extension of the rigid guide section thereby giving the articulating wire passer a gun-like appearance.

9. A wire passer system for passing a surgical wire around a bone, the wire passer system comprising:

a deployment assembly comprising a gripping section, a rigid guide section coupled to and extending forward from the gripping section, and a push rod configured to move forward when the deployment assembly is actuated;

a flexible push member configured to be pushed by the push rod when the deployment assembly is actuated;

a pointed tip member configured to be pushed by the flexible push member when the deployment assembly is actuated; and a surgical wire having a first end coupled to the pointed tip member and a main body extending through an aperture of the flexible push member, wherein the flexible push member is configured to bend around the bone and push the pointed tip member around the bone when the deployment assembly is actuated.

10. The wire passer system of claim 9, wherein the flexible push member is configured to bend when passed around the bone.

11. The wire passer system of claim 10, wherein the flexible push member comprises at least five segments pivotably connected to each other in series by a plurality of pivot points, wherein each segment of the flexible push member comprises an aperture, wherein each pivot point comprises a living hinge segment positioned above a respective aperture, and wherein the main body of the surgical wire extends through the the apertures of the flexible push member.

12. The wire passer system of claim 9, wherein the pointed tip member comprises a first securement mechanism coupling the first end of the surgical wire to the pointed tip member, and where the pointed tip member comprises a second securement mechanism for coupling a second portion of the surgical wire to the pointed tip member.

13. The wire passer system of claim 12, wherein the second securement mechanism comprises a through-opening and a set screw, wherein the through-opening is configured to receive the second portion of the surgical wire and the set screw is configured to secure the second portion of the surgical wire to the pointed tip member when the set screw is tightened against the second portion of the surgical wire.

14. The wire passer system of claim 9, wherein the flexible push member is a monolithic body formed of a resilient synthetic resin material and the pointed tip member is formed of a stainless-steel material.

15. A surgical method for passing a surgical wire around a bone, the surgical method comprising the steps of:

a) loading a flexible push member, a tip member, a surgical wire, and a pusher into a deployment assembly of an articulating wire passer with the surgical wire passing through a longitudinal passageway of the flexible push member, wherein the tip member is coupled to the surgical wire;

b) actuating the deployment assembly to push the pusher and thereby push the tip member and at least a portion of the surgical wire and the flexible push member out and at least partially around the bone;

c) while the surgical wire is extending at least partially around the bone, decoupling the deployment assembly and the flexible push member from the tip member and the surgical wire;

d) forming a tightened loop of the surgical wire around the bone; and e) securing the tightened loop of surgical wire around the bone by coupling a second portion of the surgical wire to the tip member.

16. The surgical method of claim 15, wherein the deployment assembly further comprises a handle and a rigid guide section coupled to and extending forward from the handle to give the deployment assembly a gun-like shape, and wherein during step b) the flexible push member is guided by the rigid guide section.

17. The surgical method of claim 15, wherein the tip member has a broad back end that is pushed by the flexible push member during step b), and wherein the tip member has a narrow front end that leads the tip member and the flexible push member around the bone during step b).

18. The surgical method of claim 15, wherein step b) includes causing the flexible push member to bend around the bone.

19. The surgical method of claim 18, wherein the flexible push member is formed of a monolithic piece of resilient material.

20. The surgical method of claim 18, wherein during step b), bending of the flexible push member around the bone is at least partially caused by tension in the surgical wire.

21. The surgical method of claim 15, further comprising, subsequent to step e), closing a surgical incision while the surgical wire and the tip member remain in the body.

22. The surgical method of claim 15, further comprising, prior to step a), providing the tip member and the surgical wire in a pre-assembled configuration with a first end of the surgical wire being coupled to the tip member.

23. The surgical method of claim 15, further comprising, prior to step a), opening one or more sterile packages containing the flexible push member, the tip member, and the surgical wire.

24. The surgical method of claim 15, further comprising, subsequent to step c), disposing of the flexible push member after a single use.

25. The surgical method of claim 15, wherein step d) includes extending a second portion of the surgical wire through an opening in the tip member.

26. The surgical method of claim 25, wherein step e) includes tightening a set screw of the tip member against the second portion of the surgical wire.

27. A surgical kit for use in treating subtrochanteric and/or periprosthetic bone fractures, the surgical kit comprising:
the articulating wire passer of claim 1; and
a single-use sterile package containing a surgical wire and a tip member, wherein the tip member comprises a broad back end and a narrow front end, wherein the surgical wire has a first end coupled to the back end of the tip member, and wherein said narrow front of said tip member is configured to be pushed around a fractured bone.

28. The surgical kit of claim 27 wherein the articulable member is configured to engage the back of the tip member and push the tip member around the fractured bone.

29. The surgical kit of claim 28, wherein the articulable member is provided in the same sterile package as the surgical wire and the tip member.

30. The surgical kit of claim 27, wherein the tip member comprises a securement mechanism for receiving and holding a second portion of the surgical wire to thereby form a secure loop of the surgical wire.

31. The surgical kit of claim 30, wherein the securement mechanism comprises a through-opening and a set screw, wherein the through-opening is configured to receive the second portion of the surgical wire, wherein the set screw is configured to clamp the second portion of the surgical wire in the through-opening when the set screw is tightened.

* * * * *